United States Patent
Chin et al.

(10) Patent No.: US 9,193,068 B2
(45) Date of Patent: Nov. 24, 2015

(54) STRUCTURAL ASSESSMENT, MAINTENANCE, AND REPAIR APPARATUSES AND METHODS

(71) Applicant: Elwha LLC, Bellevue, WA (US)

(72) Inventors: Hon Wah Chin, Palo Alto, CA (US); William D. Duncan, Kirkland, WA (US); Roderick A. Hyde, Redmond, WA (US); Jordin T. Kare, Seattle, WA (US); Tony S. Pan, Cambridge, MA (US); David B. Tuckerman, Lafayette, CA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 14/091,150

(22) Filed: Nov. 26, 2013

(65) Prior Publication Data

US 2015/0148955 A1 May 28, 2015

(51) Int. Cl.
*B25J 9/16* (2006.01)
*G01N 27/90* (2006.01)
(Continued)

(52) U.S. Cl.
CPC .............. *B25J 9/1602* (2013.01); *B25J 9/162* (2013.01); *B25J 9/1689* (2013.01);
(Continued)

(58) Field of Classification Search
CPC .......... B25J 19/021; B25J 5/007; B25J 9/162; B25J 9/1689; G06K 9/00624; G06K 9/00664; G01N 21/8806; G01N 27/902; G05B 2219/40194; G05B 2219/40298; G05B 2219/40307; G05B 2219/45084; G05D 1/0027; G05D 1/0094; G07C 5/008
USPC ........................ 700/246, 247, 248, 258; 901/1
See application file for complete search history.

(56) References Cited

U.S. PATENT DOCUMENTS

| 5,468,099 | A | | 11/1995 | Wheetley et al. |
| 5,790,620 | A | * | 8/1998 | Okazaki et al. ............... 376/305 |

(Continued)

FOREIGN PATENT DOCUMENTS

| JP | 2010-186819 A | 8/2010 |
| KR | 2011-0024946 A | 3/2011 |

(Continued)

OTHER PUBLICATIONS

Choset et al., Bridge Inspection with Serpentine Robots, Transportation Research Board of the National Academies, Innovations Deserving Exploratory Analysis Programs, Final Report for Highway IDEA Project 56, Oct. 2000, 15 pages.

(Continued)

*Primary Examiner* — Jason Holloway
(74) *Attorney, Agent, or Firm* — Foley & Lardner LLP (57) ABSTRACT

Systems and methods for cleaning a structure via a robot are described. The system includes a first robot and a second robot. The first robot includes a body, a tool arm, a sensor coupled, a drive system configured to allow vertical and inverted positioning of the first robot, a transceiver, and a controller. The second robot similarly includes a body, a drive system configured to allow positioning of the second robot, a transceiver, and a controller. The system includes a base station in communication with the first robot via the first robot transceiver and/or in communication with the second robot via the second robot transceiver. The first robot is configured to autonomously perform a maintenance task on the structure. The second robot is configured to autonomously provide a support service to the first robot during the maintenance task. The first robot is configured to communicate with the second robot.

24 Claims, 7 Drawing Sheets

(51) Int. Cl.
*G01N 21/88* (2006.01)
*G07C 5/00* (2006.01)
*G06K 9/00* (2006.01)
*B25J 19/02* (2006.01)

(52) U.S. Cl.
CPC ......... *G01N 21/8806* (2013.01); *G01N 27/902* (2013.01); *G07C 5/008* (2013.01); *B25J 19/021* (2013.01); *G05B 2219/40194* (2013.01); *G05B 2219/40298* (2013.01); *G05B 2219/45084* (2013.01); *G06K 9/00624* (2013.01); *G06K 9/00664* (2013.01); *Y10S 901/01* (2013.01); *Y10S 901/41* (2013.01); *Y10S 901/46* (2013.01)

(56) References Cited

U.S. PATENT DOCUMENTS

| | | | | |
|---|---|---|---|---|
| 5,809,099 | A * | 9/1998 | Kim et al. | G21C 17/013 250/559.33 |
| 5,947,051 | A | 9/1999 | Geiger | |
| 6,049,586 | A * | 4/2000 | Kitaguchi et al. | 378/57 |
| 6,112,809 | A | 9/2000 | Angle | |
| 6,288,358 | B1 | 9/2001 | Dulaney et al. | |
| 6,507,163 | B1 * | 1/2003 | Allen | 318/560 |
| 6,528,763 | B1 | 3/2003 | Lahram et al. | |
| 6,867,390 | B2 | 3/2005 | Clauer et al. | |
| 7,206,706 | B2 | 4/2007 | Wang et al. | |
| 7,267,019 | B2 * | 9/2007 | Morris et al. | 73/865.8 |
| 7,860,680 | B2 | 12/2010 | Arms et al. | |
| 8,046,101 | B2 * | 10/2011 | Hisatani et al. | B08B 1/00 700/248 |
| 8,474,553 | B1 | 7/2013 | Peyvandi et al. | |
| 2001/0013434 | A1 | 8/2001 | Hopkins | |
| 2003/0234730 | A1 | 12/2003 | Arms et al. | |
| 2006/0261771 | A1 * | 11/2006 | Anhalt et al. | 318/568.12 |
| 2006/0290779 | A1 * | 12/2006 | Reverte et al. | 348/84 |
| 2008/0109187 | A1 | 5/2008 | Kollgaard et al. | |
| 2008/0257615 | A1 | 10/2008 | Xie et al. | |
| 2008/0278151 | A1 | 11/2008 | Wang et al. | |
| 2008/0300742 | A1 | 12/2008 | Weaver et al. | |
| 2009/0163929 | A1 * | 6/2009 | Yeung et al. | 606/130 |
| 2010/0030378 | A1 | 2/2010 | Choi et al. | |
| 2010/0049367 | A1 * | 2/2010 | Yang | 700/259 |
| 2010/0235037 | A1 | 9/2010 | Vian et al. | |
| 2011/0093139 | A1 * | 4/2011 | Arms et al. | 701/2 |
| 2011/0106313 | A1 * | 5/2011 | Lee et al. | 700/259 |
| 2012/0116583 | A1 | 5/2012 | Beard et al. | |
| 2012/0215348 | A1 | 8/2012 | Skrinde | |
| 2013/0011234 | A1 * | 1/2013 | Pretlove et al. | B25J 5/005 414/749.1 |
| 2013/0140801 | A1 * | 6/2013 | Schlee et al. | B62D 57/024 280/762 |
| 2013/0289766 | A1 * | 10/2013 | Hafenrichter et al. | B25J 9/02 700/245 |

FOREIGN PATENT DOCUMENTS

| | | |
|---|---|---|
| KR | 2012-0068330 A | 6/2012 |
| KR | 2013-0025526 A | 3/2013 |
| KR | 2013-0105130 A | 9/2013 |

OTHER PUBLICATIONS

Pettinaro et al., Swarm Robotics: A Different Approach to Service Robotics, Proceedings of the 33rd ISR (International Symposium on Robotics) Oct. 7-11, 2002, 6 pages.

ZR-1 Robot System for Inspection and Maintenance/Repair, Zetec, Inc., retrieved from http://www.zetec.com/2010/06/zr-1-robot/ Feb. 6, 2014, 3 pages.

PCT International Search Report; International App. No. PCT/US2014/067108; Mar. 13, 2015; pp. 1-6.

* cited by examiner

STRUCTURAL ASSESSMENT, MAINTENANCE, AND REPAIR APPARATUSES AND METHODS

CROSS-REFERENCE TO RELATED APPLICATIONS

This application is related to U.S. patent application Ser. No. 14/090,725, titled "Structural Assessment, Maintenance, and Repair Apparatuses and Methods," filed Nov. 26, 2013, which is hereby incorporated by reference in its entirety.

BACKGROUND

Large structures, such as buildings, bridges, and oil rigs, require regular maintenance and inspection. Typically, regular inspection and maintenance is performed by human crews. However, human crews have physical limits and may be expensive to employ. For example, reaching certain areas of the structures, such as the top trusses and underwater supports of a bridge, may be difficult and dangerous for human inspection and maintenance crews. Further, some areas of structures, including tight spaces, may be completely inaccessible by human inspection and maintenance crews. Still further, human inspection and maintenance crews are susceptible to inclement weather conditions, which may hamper and delay maintenance and inspection operations.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

One embodiment relates to a system for maintaining a structure. The system includes a first robot. The first robot includes a first robot body, a first robot tool arm coupled to the first robot body, a first robot sensor coupled to the first robot body, a first robot drive system configured to allow positioning of the first robot along the structure, including inverted positioning and vertical positioning, a first robot transceiver coupled to the first robot body, and a first robot controller coupled to the first robot body. The system further includes a second robot. The second robot includes a second robot body, a second robot drive system configured to allow positioning of the second robot along the structure, a second robot transceiver coupled to the second robot body, and a second robot controller coupled to the second robot body. The system includes a base station in communication with the first robot via the first robot transceiver and/or in communication with the second robot via the second robot transceiver. The first robot is configured to autonomously perform a maintenance task on the structure. The second robot is configured to autonomously provide a support service to the first robot during the maintenance task. The first robot is configured to communicate with the second robot.

Another embodiment relates to a method of performing a maintenance task on a structure via a robot. The method includes moving to an area of the structure through a drive system of the robot. The method further includes detecting a characteristic of a portion of the structure through a sensor of the robot, and, in response to detecting the characteristic, identifying a maintenance task. The method includes performing the maintenance task through a tool mounted to a tool arm of the robot. The method further includes documenting the performance of the maintenance task.

Still another embodiment relates to a method of painting a structure via a robot. The method includes receiving a command to paint at least a portion of the structure via a transceiver of the robot. The method further includes analyzing the command via a controller of the robot, wherein the analyzing includes identifying the portion of the structure where painting is to be performed. The method includes moving to the portion of the structure through a drive system of the robot. The method further includes identifying a first area of the portion of the structure as a target for painting. The method includes determining that a second area proximate the structure is not occupied by an object through a sensor of the robot, wherein the second area of the structure is at risk of being hit by an overspray of paint. The method includes, after determining that the second area proximate the structure is not occupied by the object, painting the first area of the structure through a tool of the robot.

Yet another embodiment relates to a method of detecting and repairing corrosion on a structure via a robot. The method includes receiving a command to locate and repair corrosion on the structure through a transceiver of the robot. The method further includes analyzing the command through a controller of the robot. The method includes roving to an area of the structure. The method further includes identifying, via a first sensor of the robot, an area of corrosion on the structure. The method includes cleaning the area with an abrasive tool mounted to the robot. The method further includes, after cleaning the area, painting the area with a painting tool of the robot.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
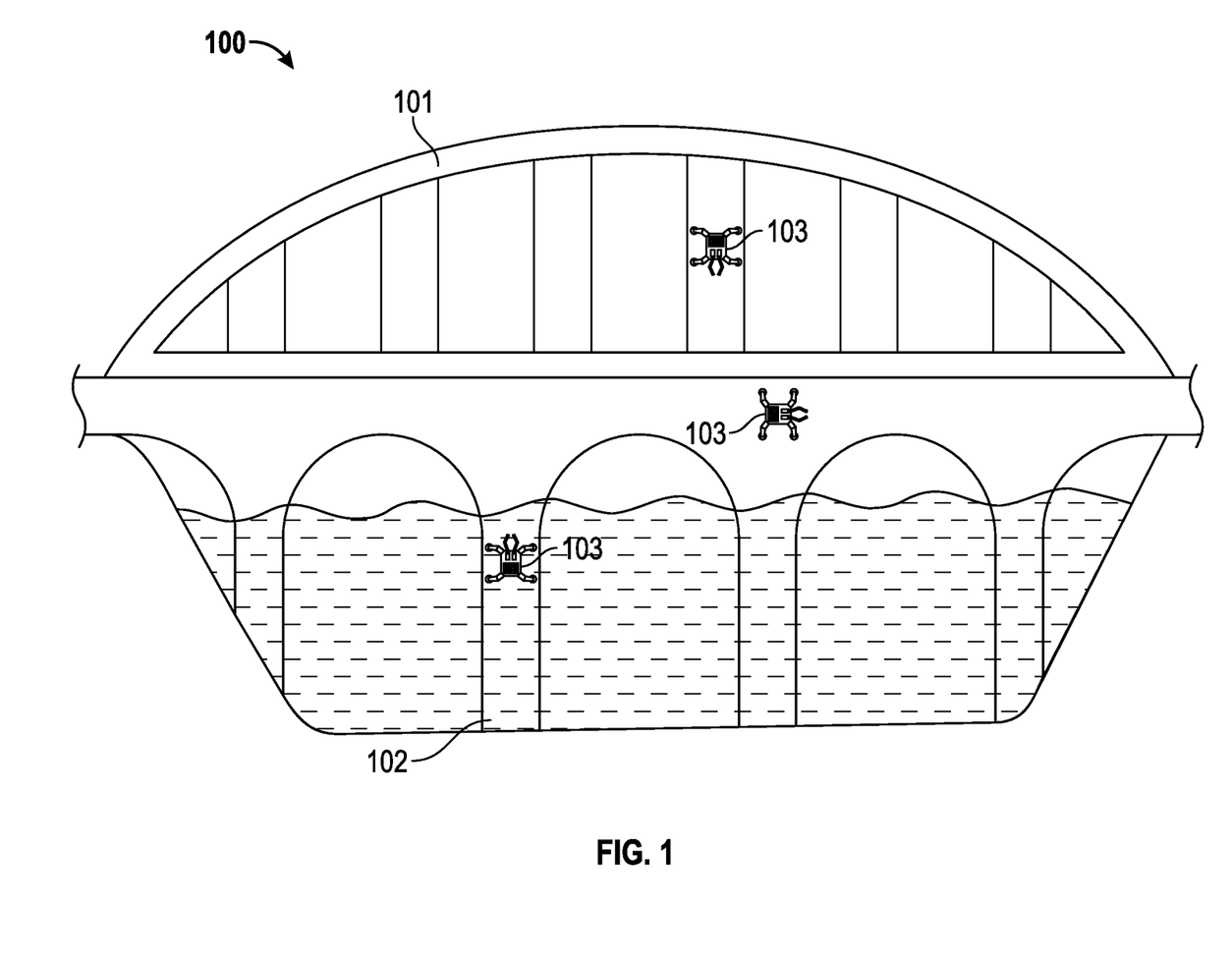
FIG. 1 is a view of a bridge having maintenance robots according to an embodiment.

Referring to FIG. 1, bridge 100 is shown according to one embodiment. Bridge 100 includes above water portions 101 and below water portions 102. A number of robots 103 are shown on bridge 100. Robots 103 affix to bridge 100 and move about bridge 100. Robots 103 affix to bridge 100 through various methods, including, but not limited to, suction devices, dry adhesives, adhesives, mechanical grippers, magnetism, electroadhesion, treads, and wheels. Some robots 103 may be configured for underwater use, in which case robots 103 include underwater propulsion mechanisms such as propellers and/or water jets. Robots 103 are equipped with sensors and tools such that robots 103 can autonomously inspect, clean, and/or repair bridge 100 depending on the tool configuration and received programming instructions. The tools and sensors may be mounted to tool arms or to the body of each robot 103. The tools and sensors may be removably mounted to the tool arms and/or to the body of each robot such that the tools and sensors are replaceable. In such an arrangement, robots 103 are reconfigurable for different tasks. Robots 103 may communicate (e.g., wirelessly) with other robots and/or with a base station (e.g., a control vehicle having human operators, a fixed control facility, etc.). Robots 103 may come in a variety of sizes and may be used to inspect a variety of structures. The details of robots 103 are discussed in further detail below.

Figure 2:
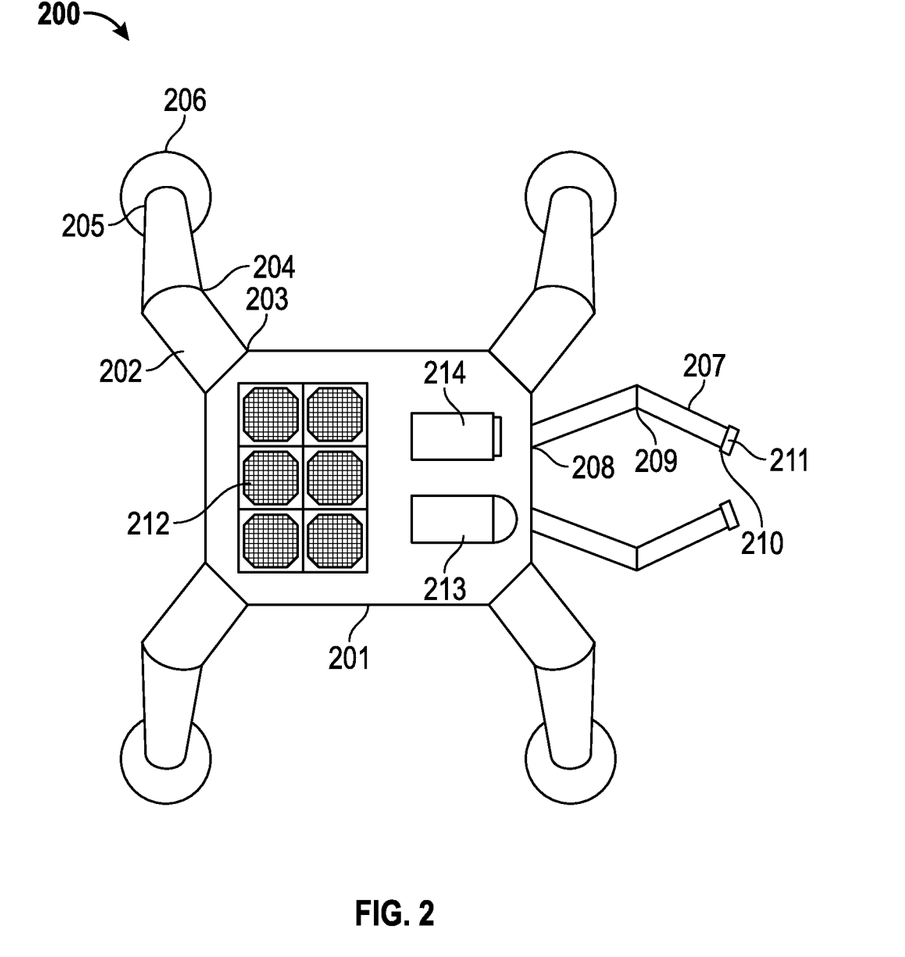
FIG. 2 is a view of a robot according to an embodiment.

Referring to FIG. 2, robot 200 is shown according to one embodiment. Robot 200 includes main body 201. Main body 201 may be constructed from metal (e.g., steel, aluminum, titanium, or alloys thereof), plastics, composites (e.g., fiberglass, carbon fiber, etc.), or a combination thereof. The various components of robot 200 are coupled to main body 201. Robot 200 is shown as having four legs 202. In alternative arrangements, robot 200 may include a different number of legs 202 (e.g., six legs, eight legs, ten legs, etc.). In the embodiment of FIG. 2, each leg 202 includes three joints 203, 204, and 205, which enable movement of the various parts of leg 202. Joints 203, 204, and 205 may be universal joints that allow for three axes of movement. Each joint 203, 204, and 205 includes at least one motor (e.g., a servo motor) for controlled relative movement of parts of leg 202 about joints 203, 204, and 205.

In the embodiment of FIG. 2, each leg 202 includes surface gripping element 206. Element 206 is coupled to leg 202. Element 206 is configured to removably affix robot 200 to a surface of a structure (e.g., a beam of bridge 100) such that robot 200 can move along structures having a steep incline, vertical structures (e.g., a vertical beam of bridge 100, a wall of a building, etc.), or in an inverted manner (along the underside of bridge 100, on the ceiling of a building, etc.). Accordingly, element 206 creates an attraction force between element 206 and a surface.

The attraction force may be achieved using a variety of techniques. In some arrangements, element 206 includes a dry adhesive. A dry adhesive uses microscopic setae and spatulae that, when pressed directly into a surface, create an adhesion force capable of supporting a load on a vertical surface. Further details of how dry adhesives function can be found in U.S. Pat. No. 8,398,909 to Sitti et al., entitled "DRY ADHESIVES AND METHODS OF MAKING DRY ADHESIVES," dated Mar. 19, 2013. In other arrangements, element 206 may include a suction device. In such an arrangement, a vacuum creates a controllable suction force such that elements 206 are selectively secured to a surface. The amount of electrical power provided to the vacuum may be increased or decreased depending on the amount of suction force required to secure element 206 to the surface. In another arrangement, element 206 includes an electromagnet. In such an arrangement, the electromagnet is selectively powered such that elements 206 are selectively secured to a surface via magnetic force. The amount of electrical power provided to the electromagnet may be increased or decreased depending on the magnetic force required to secure element 206 to the surface. In yet another arrangement, element 206 includes at least one electrode for creating electrostatic adhesion between element 206 and a surface. When powered, the electrode may pass electrons from element 206 to a conductive surface (e.g., a steel beam of bridge 100), which creates an electrostatic attractive force between element 206 and the surface. In another arrangement, element 206 includes a mechanical gripping appendage designed to grasp the surface (e.g., by at least partially encircling it, by inserting screws or pitons, etc.). In another arrangement, element 206 includes a combination of any of the above the above described gripping mechanisms (e.g., a suction mechanism, a dry adhesive, a mechanical gripper, and an electromagnet).

Robot 200 includes arms 207. Arms 207 are similar to legs 202. Although robot 200 is drawn as having two arms 207, it should be understood that any number of arms may be used (e.g., one arm, three arms, four arms, etc.). Further, arms may be mounted to any side of body 201. Arms 207 include joints 208, 209, and 210. Joints 208, 209, and 210 may be universal joints that allow for three axes of movement. Each joint 208, 209, and 210 includes at least one motor (e.g., a servo motor) for controlled relative movement of parts arm 207 about joints 208, 209, and 210. Each arm 207 includes tool connector 211. Tool connector 211 is configured to removably receive a variety of tools (e.g., a welder, a brush, a hammer, a drill, shears, a fastener driver, a paint sprayer, an abrasive blaster, etc.) and/or sensors (ultrasound sensors, x-ray sensor, stress sensors, cameras, acoustic sensors, etc.) in an interchangeable manner. Accordingly, robot 200 can be configured to perform a variety of tasks, such as structure inspection, structure cleaning, structure painting, and structure repair. Tool connector 211 may be a proprietary connector.

Robot 200 also includes additional components coupled to body 201. In some arrangements, robot 200 includes solar panel 212 coupled to body 201. Solar panel 212 provides operational power to robot 200 and/or charges batteries within body 201. In certain arrangements, light 213 is coupled to body 201. Light 213 illuminates a workspace of robot 200 during dimly lit or nighttime operations. Light 213 may provide spectrally defined illumination, having specified colors or spectral bands (infrared, visible, ultraviolet) selected to improve imaging of a feature needing maintenance (e.g., a corroded portion of the surface), or of the maintenance progress (e.g., detection of a paint or surface treatment). Light 213 may provide multi-spectral light or polarized light for multi-spectral imaging or polarized imaging of a component of the structure. Light 213 assists robot 200 with low-light image and video capturing through camera 214. Camera 214 is coupled to body 201. In alternative arrangements, camera 214 may be coupled to tool connector 211 of an arm 207. In some configurations, robot 200 includes multiple cameras, which enable stereoscopic three-dimensional image and video capture.

Figure 3:
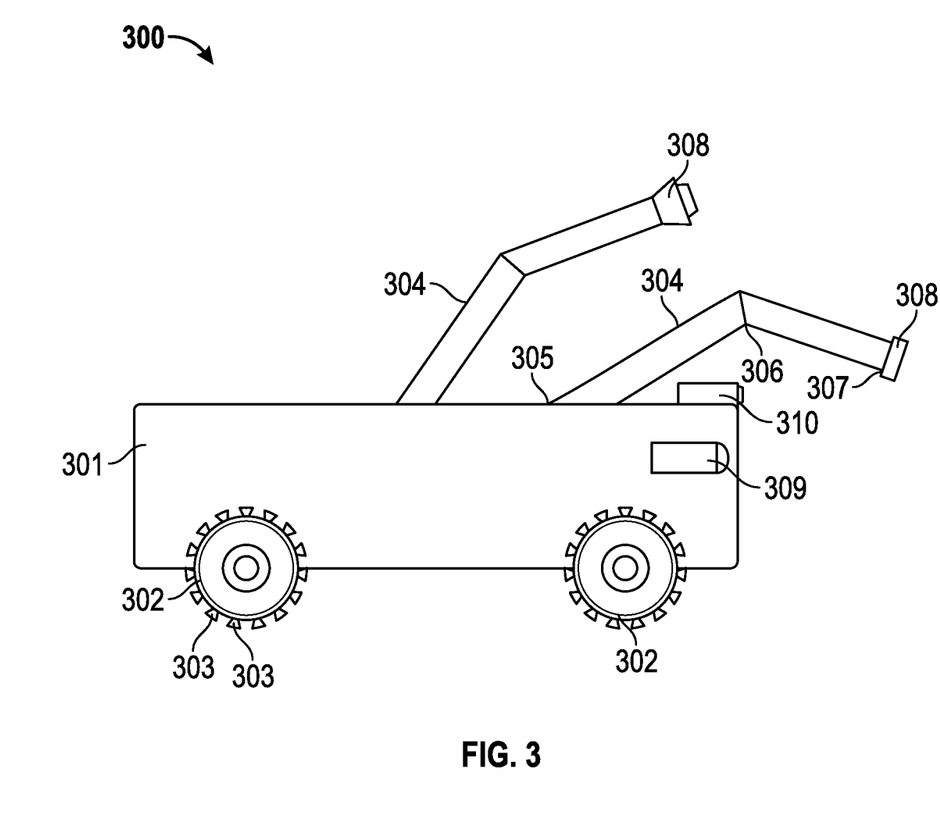
FIG. 3 is a view of a robot according to an embodiment.

Referring to FIG. 3, robot 300 is shown according to one embodiment. Robot 300 is similar to robot 200. Robot 300 includes main body 301. Main body 301 may be constructed from metal (e.g., steel, aluminum, titanium, or alloys thereof), plastics, composites (e.g., fiberglass, carbon fiber, etc.), or a combination thereof. The various components of robot 300 are coupled to main body 301. Unlike robot 200, robot 300 does not include legs. Instead, robot 300 includes wheels 302. Although robot 300 is shown as including four wheels, robot 300 may include three wheels or more than four wheels.

Each wheel 302 includes a plurality of surface gripping elements 303. Element 303 is coupled to leg 202. Elements 303 are configured to removably affix robot 300 to a surface of a structure (e.g., a beam of bridge 100) such that robot 300 can move along structures having a steep incline, vertical structures (e.g., a vertical beam of bridge 100, a wall of a building, etc.), or in an inverted manner (along the underside of bridge 100, on the ceiling of a building, etc.). Accordingly, elements 303 create an attraction force between elements 303 and a surface.

The attraction force may be achieved using a variety of techniques. Elements 303 may include the same components as discussed above with elements 206. Accordingly, elements 303 may include a dry adhesive, a suction mechanism, a mechanical gripper, an electromagnet, at least one electrode for creating electrostatic adhesion between element 303 and a surface, or a combination of the above the above described gripping mechanisms (e.g., a suction mechanism, a dry adhesive, and an electro-magnet).

In the embodiment of FIG. 3, robot 300 includes arms 304. Arms 304 are similar to arms 207 of robot 200. Although robot 300 is drawn as having two arms 304, it should be understood that any number of arms may be used. Further, arms may be mounted to any side of body 301. Arms 304 include joints 305, 306, and 307. Joints 305, 306, and 307 may be universal joints that allow for three axes of movement. Each joint 305, 306, and 307 includes at least one motor (e.g., a servo motor) for controlled relative movement of parts arm 304 about joints 305, 306, and 307. Each arm 304 includes tool connector 308. Tool connector 308 is configured to removably receive a variety of tools (e.g., a welder, a brush, a hammer, a drill, shears, a fastening driver, paint sprayer, sandblaster, etc.) and/or sensors (ultrasound sensors, x-ray sensor, stress sensors, cameras, acoustic sensors, etc.) in an interchangeable manner. Accordingly, robot 300 can be configured to perform a variety of tasks, such as structure inspection, structure cleaning, structure painting, and structure repair. Tool connector 308 may be a proprietary connector.

Robot 300 also includes additional components coupled to body 301. In certain arrangements, light 309 is coupled to body 301. Light 309 illuminates a workspace of robot 300 during dimly lit or nighttime operations. Light 309 may provide spectrally defined illumination, having specified colors or spectral bands (infrared, visible, ultraviolet) selected to improve imaging of a feature needing maintenance (e.g., a corroded portion of the surface), or of the maintenance progress (e.g., detection of a paint or surface treatment). Light 309 may provide multi-spectral light or polarized light for multi-spectral imaging or polarized imaging of a component of the structure. Light 309 assists robot 300 with low-light image and video capturing through camera 310. Camera 310 is coupled to body 301. In alternative arrangements, camera 310 may be coupled to tool connector 308 of an arm 304. In some configurations, robot 300 includes multiple cameras, which enable stereoscopic three-dimensional image and video capture.

Figure 4:
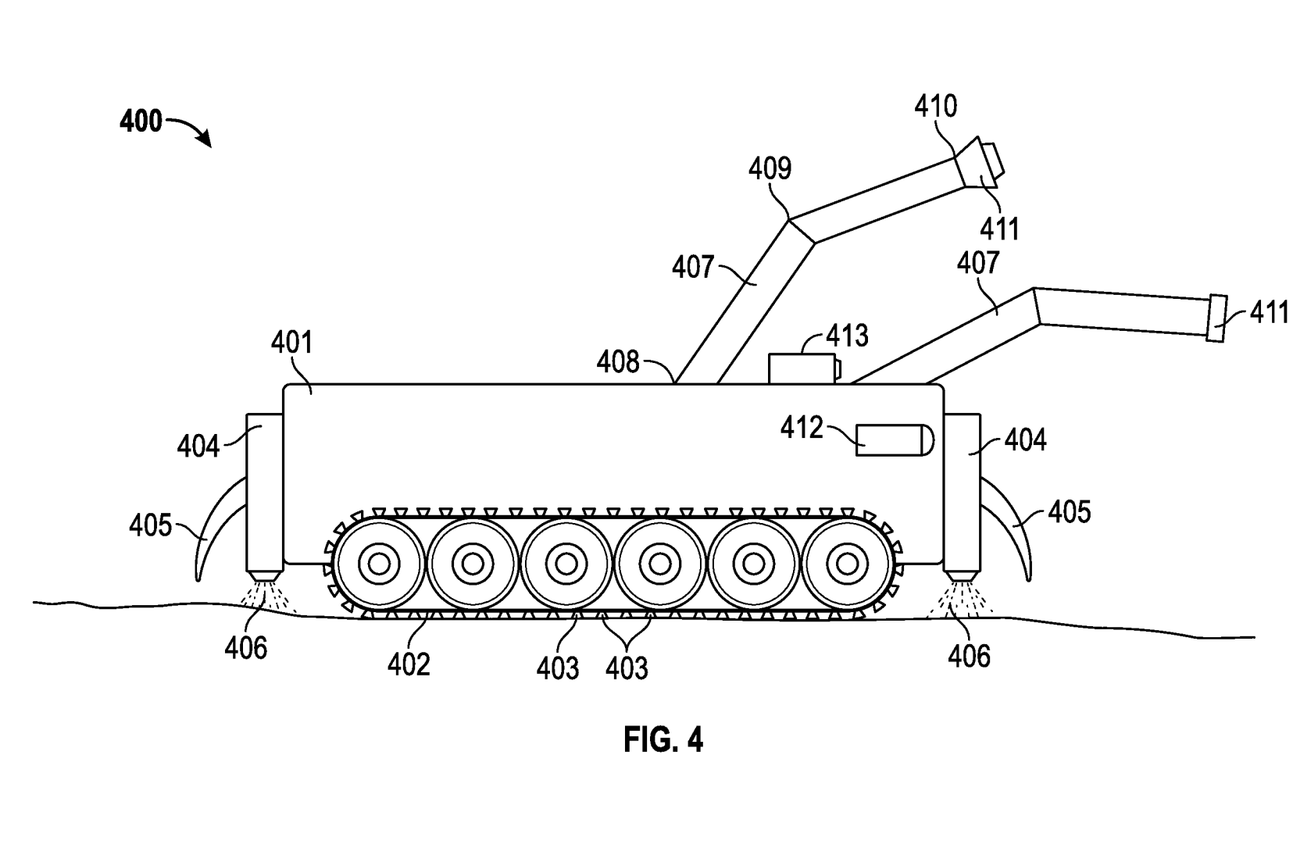
FIG. 4 is a view of a robot according to an embodiment.

Referring to FIG. 4, robot 400 is shown according to one embodiment. Robot 400 is similar to robots 300 and robot 200. Robot 400 includes main body 401. Main body 401 may be constructed from metal (e.g., steel, aluminum, titanium, or alloys thereof), plastics, composites (e.g., fiberglass, carbon fiber, etc.), or a combination thereof. The various components of robot 400 are coupled to main body 401. Unlike robots 200 or 300, robot 400 is propelled by driven track 402. Robot 400 includes any number of tracks 402 (e.g., one track, two tracks, three tracks, etc.).

In the embodiment of FIG. 4, each track 402 includes a plurality of surface gripping elements 403 coupled to tracks 402. Elements 403 are configured to removably affix robot 400 to a surface of a structure (e.g., a beam of bridge 100) such that robot 400 can move along structures having a steep incline, vertical structures (e.g., a vertical beam of bridge 100, a wall of a building, etc.), or in an inverted manner (along the underside of bridge 100, on the ceiling of a building, etc.). Accordingly, elements 403 create an attraction force between elements 403 and the surface that robot 400 is moving along.

The attraction force may be achieved using a variety of techniques. Elements 403 may include the same components as discussed above with elements 206 and 303. Accordingly, elements 403 may include a dry adhesive, a suction mechanism, a mechanical gripper, an electromagnet, at least one electrode for creating electrostatic adhesion between element 403 and a surface, or a combination of the above the above described gripping mechanisms (e.g., a suction mechanism, a dry adhesive, and an electro-magnet).

In some configurations, robot 400 includes adhesive dispensers 404 and adhesive scrapers 405. Adhesive dispensers 404 spray adhesive 406 onto a surface robot 400 is traversing. The adhesive may be sprayed between the surface of the structure and a component of the robot drive system (e.g., between track 402 and the structure). The adhesive works to adhere robot 400 to the surface. The adhesive may be a drying adhesive, a pressure sensitive adhesive, a contact adhesive, a hot adhesive, a multi-part reactive adhesive (e.g., epoxy), or a one-part reactive adhesive. Scrapers 405 are movable such that scrapers only scrape the surface when instructed. Scrapers 405 can be lowered to touch the surface such that sprayed adhesive 406 is scraped off of the surface. Dispensers 404 and scrapers 405 are provided on both sides of tracks 402 to facilitate both forwards and backwards motion of robot 400 during inclined, vertical, or inverted movement. Adhesive 406 may be used to supplement the attractive forces provided by elements 403 or may be used in place of elements 403.

Robot 400 includes arms 407. Arms 407 are similar to arms 207 and 304 of robots 200 and 300. Although robot 400 is drawn as having two arms 407, it should be understood that any number of arms may be used. Further, arms may be mounted to any side of body 401. Arms 407 include joints 408, 409, and 410. Joints 408, 409, and 410 may be universal joints that allow for three axes of movement. Each joint 408, 409, and 410 includes at least one motor (e.g., a servo motor) for controlled relative movement of parts arm 407 about joints 408, 409, and 410. Each arm 407 includes tool connector 411. Tool connector 411 is configured to removably receive a variety of tools (e.g., a welder, a brush, a hammer, a drill, shears, a fastening driver, paint sprayer, sandblaster, etc.) and/or sensors (ultrasound sensors, x-ray sensor, stress sensors, cameras, acoustic sensors, etc.) in an interchangeable manner. Accordingly, robot 400 can be configured to perform a variety of tasks, such as structure inspection, structure cleaning, structure painting, and structure repair. Tool connector 411 may be a proprietary connector.

Robot 400 also includes additional components coupled to body 401. In certain arrangements, light 412 is coupled to body 401. Light 412 illuminates a workspace of robot 400 during dimly lit or nighttime operations. Light 412 may provide spectrally defined illumination, having specified colors or spectral bands (infrared, visible, ultraviolet) selected to improve imaging of a feature needing maintenance (e.g., a corroded portion of the surface), or of the maintenance progress (e.g., detection of a paint or surface treatment). Light 412 may provide multi-spectral light or polarized light for multi-spectral imaging or polarized imaging of a component of the structure. Light 412 assists robot 400 with low-light image and video capturing through camera 413. Camera 413 is coupled to body 401. In alternative arrangements, camera 413 may be coupled to tool connector 411 of an arm 407. In some configurations, robot 400 includes multiple cameras, which enable stereoscopic three-dimensional image and video capture.

Figure 5:
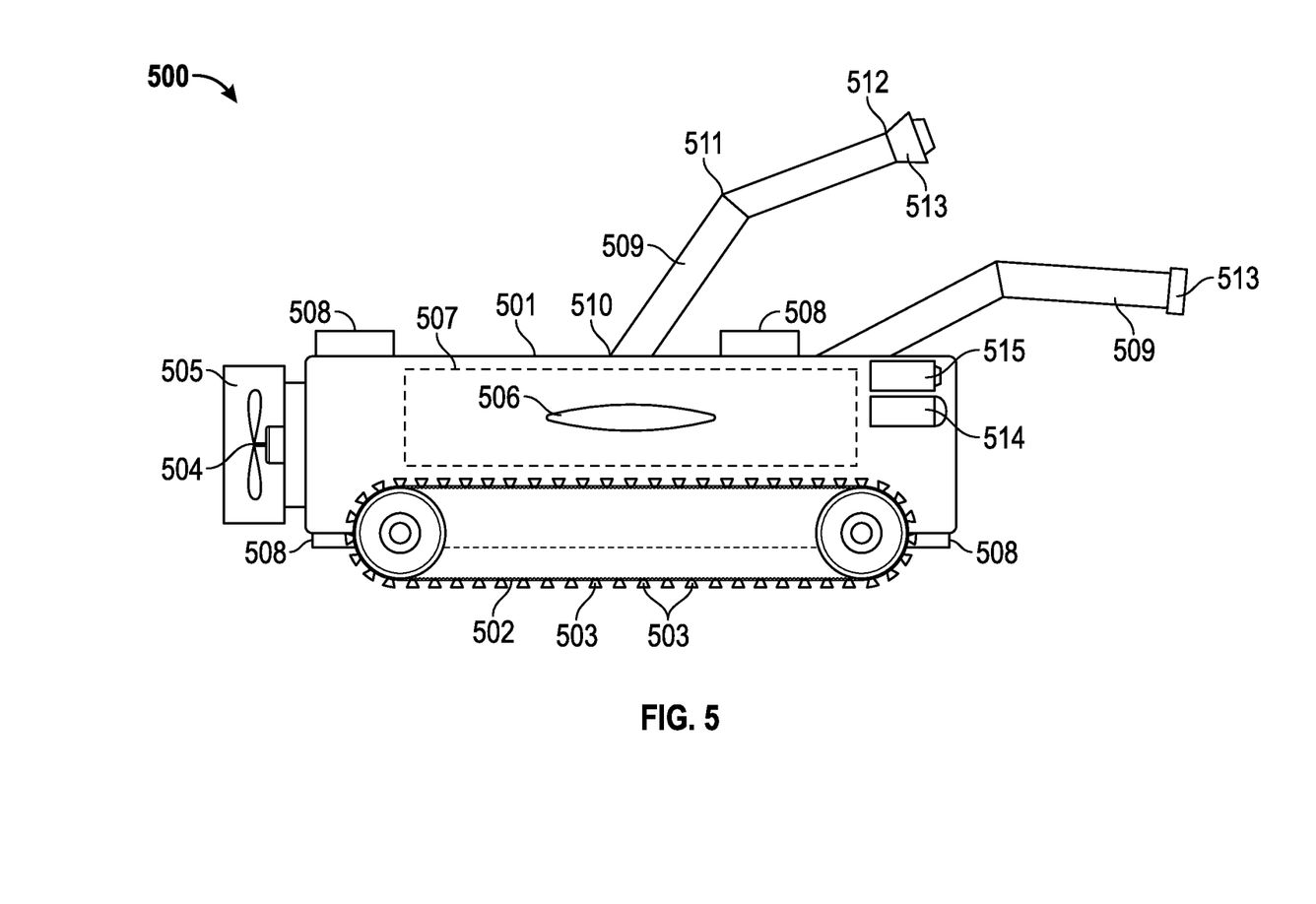
FIG. 5 is a view of a robot according to an embodiment.

Referring to FIG. 5, robot 500 is shown according to one embodiment. Robot 500 is similar to robots 200, 300, and 400. However, robot 500 is additionally configured for operation underwater. Robot 500 includes main body 301. Main body 501 may be constructed from metal (e.g., steel, aluminum, titanium, or alloys thereof), plastics, composites (e.g., fiberglass, carbon fiber, etc.), or a combination thereof. The various components of robot 500 are coupled to main body 501. Main body 501 may be water-tight to protect internal components. Alternatively, body 501 includes a separate water-tight compartment for housing electrical components (e.g., a controller, a transceiver, a battery, etc.). Robot 500 includes multiple movement mechanisms to allow robot 500 to move over ground, across structures, and underwater. Robot 500 includes a transceiver configured for communications with an external base station (located either above the water surface, or underwater). The communication between robot 500 and the extern base station may be via a cable (e.g., an optical fiber), or may be wireless (e.g., acoustic).

Robot 500 includes two tracks 502, which provide robot 500 movement over land and across structures. Although drawn as including two tracks 502, robot 500 can include any number of tracks. Each track 502 includes a plurality of surface gripping elements 503 coupled to tracks 502. Elements 503 are configured to removably affix robot 500 to a surface of a structure (e.g., a beam of bridge 100) such that robot 500 can move along structures having a steep incline, vertical structures (e.g., a vertical beam of bridge 100, a wall of a building, etc.), or in an inverted manner (along the underside of bridge 100, on the ceiling of a building, etc.). Accordingly, elements 503 create an attraction force between elements 503 and a surface.

The attraction force may be achieved using a variety of techniques. Elements 503 may include the same components as discussed above with elements 206, 303, and 403. Accordingly, elements 503 may include a dry adhesive, a suction mechanism, a mechanical gripper, an electromagnet, at least one electrode for creating electrostatic adhesion between element 503 and a surface, or a combination of the above the above described gripping mechanisms (e.g., a suction mechanism, a dry adhesive, and an electro-magnet).

Robot 500 further includes an underwater drive system having motorized propeller 504. Propeller 504 is mounted on rudder 505. Propeller 504 is rotated about main body 501 to propel robot 500. Propeller 504 can be powered in both directions to cause forward and backward movement of robot 500 underwater. To assist with underwater navigation, robot 500 further includes elevator fins 506 and ballast 507. Elevator fins 506 can be rotated with respect to body 501 to help robot 500 ascend or descend while underwater. Ballast 507 can fill with air or liquid to adjust the buoyancy of robot 500. Accordingly, ballast 500 assists robot 500 in ascending or descending while underwater. Robot 500 also includes water jets 508. Water jets 508 are individually operable. Each water jet 508 can propel a jet of water. Accordingly, water jets 508 assist robot 500 in ascending or descending while underwater. Robot 500 may be capable of navigation through liquids other than water, such as oil.

Further referring to FIG. 5, robot 500 includes arms 509. Arms 509 are similar to arms 207, 304, and 407. Although robot 500 is drawn as having two arms 509, it should be understood that any number of arms may be used. Further, arms may be mounted to any side of body 501. Arms 509 include joints 510, 511, and 512. Joints 510, 511, and 512 may be universal joints that allow for three axes of movement. Each joint 510, 511, and 512 includes at least one motor (e.g., a servo motor) for controlled relative movement of parts arm 509 about joints 510, 511, and 512. Each arm 509 includes tool connector 513. Tool connector 513 is configured to removably receive a variety of tools (e.g., a welder, a brush, a hammer, a drill, shears, a fastening driver, paint sprayer, sandblaster, etc.) and/or sensors (ultrasound sensors, x-ray sensor, stress sensors, cameras, acoustic sensors, etc.) in an interchangeable manner. Accordingly, robot 500 can be configured to perform a variety of tasks, such as structure inspection, structure cleaning, structure painting, and structure repair. Tool connector 513 may be a proprietary connector.

Robot 500 also includes additional components coupled to body 501. In certain arrangements, light 514 is coupled to body 501. Light 514 illuminates a workspace of robot 500 during dimly lit or nighttime operations. Light 514 may provide spectrally defined illumination, having specified colors or spectral bands (infrared, visible, ultraviolet) selected to improve imaging of a feature needing maintenance (e.g., a corroded portion of the surface), or of the maintenance progress (e.g., detection of a paint or surface treatment). Light 514 may provide multi-spectral light or polarized light for multi-spectral imaging or polarized imaging of a component of the structure. Light 514 also assists robot 500 with low-light image and video capturing through camera 515. Camera 515 is coupled to body 501. In alternative arrangements, camera 515 may be coupled to tool connector 513 of an arm 509. In some configurations, robot 500 includes multiple cameras, which enable stereoscopic three-dimensional image and video capture.

The machines described in FIG. 2 through FIG. 5 above provide four devices that may be used for structure inspection, cleaning, and/or repair. However, it should be understood that alternatively configured robots may be used within the scope of the contemplated invention. For example, any number and combination of tool arms, cameras, sensor arrays, and movement mechanisms may be employed.

Figure 6:
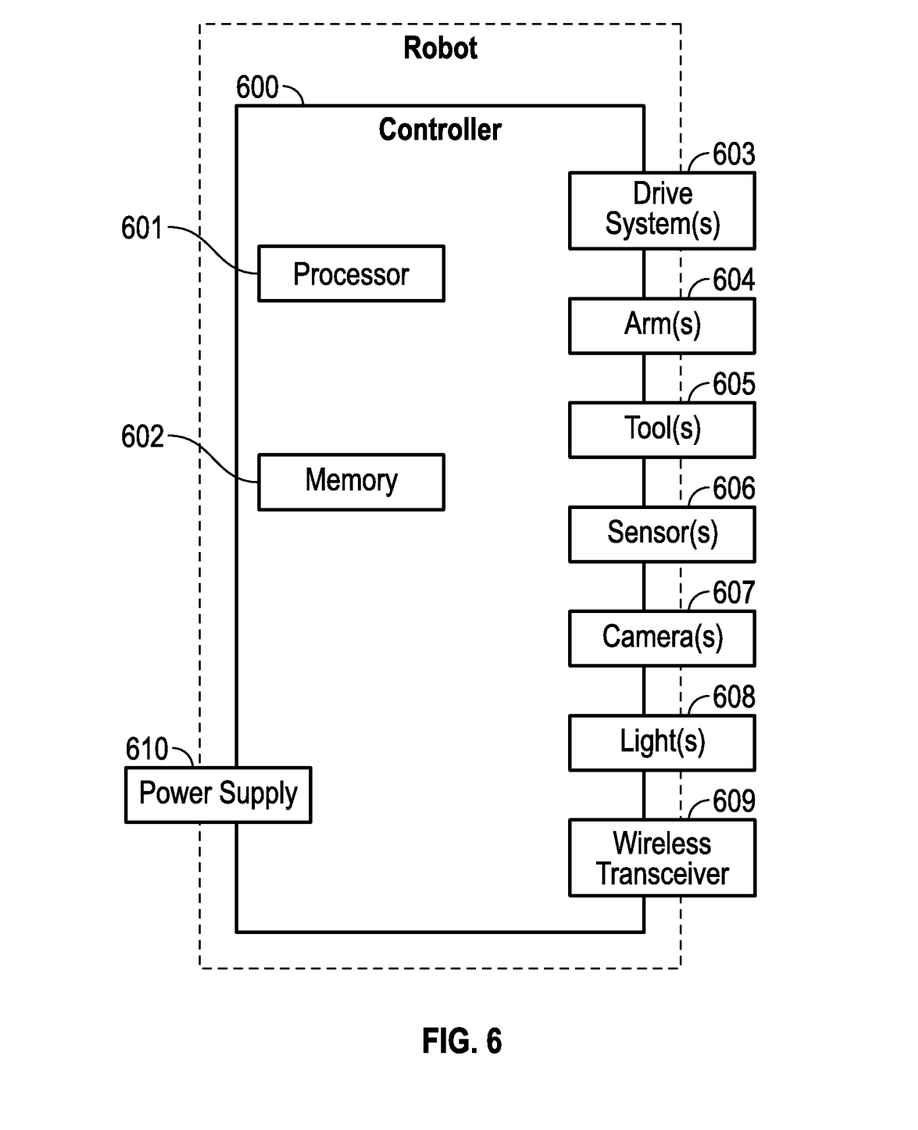
FIG. 6 is a block diagram of a controller for a robot according to an embodiment.

Referring to FIG. 6, a block diagram of controller 600 is shown according to an embodiment. Controller 600 may be used to control the operation of any of the above discussed robots (i.e., robot 200, robot 300, robot 400, or robot 500) or a similarly configured robot. Controller 600 includes processor 601 and memory 602. Memory 602 stores programming instructions that, when executed by processor 601, control the robot's operation, including the various components of the robot. Controller 600 is in electrical communication with drive system 603, arm 604, tool 605, sensor 606, camera 607, and light 608. As discussed above with respect to robots 200, 300, 400, and 500, a robot may have a plurality of any of drive systems, arms, tools, sensors, cameras, and lights. In such arrangements, controller 600 is in electrical communication with each of the plurality of components.

Controller 600 includes wireless transceiver 609. Wireless transceiver 609 may be integrated into controller 600 (e.g., controller may be a system-on-chip including processor 601, memory 602, and wireless transceiver 609 on a single chip) or a separate component in electrical communication with controller 600. Controller 600 receives operating instructions from an outside source through wireless transceiver 609. For example, controller 600 can receive operating instructions from an operator at a control station. The operating instructions may relate to remote control instructions (i.e., when the operator is controlling all of the functions of the robot) or autonomous operation instructions to perform a task with little or no operator intervention (e.g., autonomous inspections, autonomous repainting, autonomous repair, etc.). Still further, controller 600 can communicate with other robots through wireless transceiver 609. In some situations, robots are instructed to work together on the same or related tasks. Accordingly, the robots may need to communicate with each other. For example, a first robot may be instructed to inspect a structure, and a second robot may be instructed to repair defects in the structure found by the first robot. In such a configuration, the first robot will transmit defect information (e.g., type of defect, location of defect on the structure, defect repair strategy, etc.) to the second robot. In some embodiments the first robot and the second robot may communicate with each other wirelessly (e.g., via radio-frequency, acoustics, optics, etc.); in other embodiments they may communicate via a cable (e.g., an optical fiber, a wire, coaxial cable, etc.). In some embodiments, a first robot may communication with an external base station via a wireless transceiver, such that the first robot may relay communications designated for the second robot from the external base station to the second robot, or may relay communications from the second robot to the external base station. As an additional example, a pair of robots can be used where a first robot performs assigned maintenance tasks (e.g., inspection and repair) and a second robot provides a support service to the first robot. The support service may include the carrying of supplies to be used by the first robot (e.g., additional tools, abrasives for sand blasting, paint for painting, additional batteries for extended operation, etc.), assisting with tool change operations for the first robot, charging the first robot's batteries through a charging port of the second robot, or a similar ancillary task. In such a configuration, the first robot will transmit requests to the second robot.

Controller 600 receives operational electrical power from power supply 610. Power supply 610 provides to controller 600 and all components of the robot. Power supply 610 may be any suitable power source, including, but not limited to, a battery, a generator, a solar power source, grid power, or a combination thereof. In arrangements where power supply 610 includes a rechargeable battery, the battery may be charged during operation through another power source (e.g., a generator, a solar panel, grid power, etc.) or through inductive charging (i.e., the robot can drive over an inductive charger configured to charge the rechargeable battery).

Figure 7:
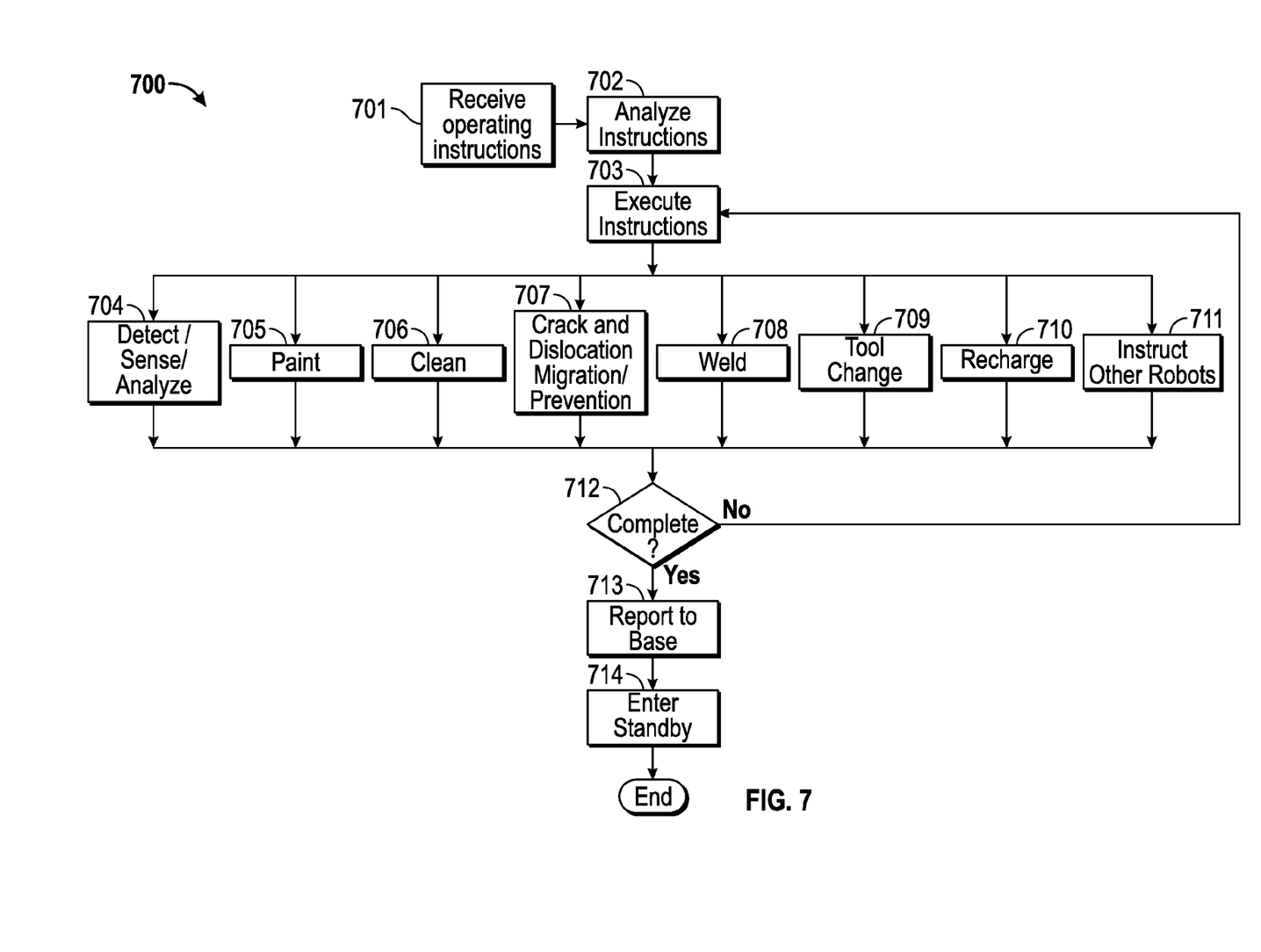
FIG. 7 is a flow diagram of a method of performing a function via a robot is shown according to an embodiment.

Referring to FIG. 7, method 700 of performing a function via a robot is shown according to an embodiment. Method 700 may be employed by any of the above described robots (i.e., robot 103, robot 200, robot 300, robot 400, and/or robot 500) or another robot configured to inspect and/or perform repairs on a structure.

The robot receives operating instructions (701). Operating instructions may be received through a wireless transceiver of the robot. The operating instructions may originate from a base station (e.g., a human operator at the base station) or from another robot (e.g., during a multi-robot operation). After receiving the instructions, the robot analyzes the operating instructions (702). The controller of the robot parses the received instructions to determine the individual tasks of the instructions, where the tasks are to be performed (e.g., what area of the structure the robot should move to), and when the tasks are to be performed. The instructions may relate to an on-demand task (e.g., repainting a portion of a structure upon receipt of the instructions), a scheduled task (e.g., repainting a portion of a structure at a designated time and date), or performing a task autonomously based on sensor results (e.g., repainting a portion of a structure based on sensor feedback indicating that the portion requires repainting).

After analyzing the instructions, the robot executes the operating instructions (703). The robot executes the instructions at the proper location on the structure (e.g., by moving to the target location of the structure) at the time of execution. The instructions can include any combination of tasks, including, but not limited to: detecting, sensing, and analyzing features of the structure (704), painting (705), cleaning (706), crack dislocation, migration, or prevention (707), welding (708), performing a tool change (709), charging (710), and/or communicating with other robots (711). The above discussed tasks are discussed below in greater detail.

Further referring to FIG. 7, the robot determines if the operating instructions have been completed (712). If the operating instructions have not been completed, method 700 returns to 703 for continued execution of the operating instructions. If the operating instructions have been completed, the robot sends a final report to the base station (713). In some embodiments, progress reports may be sent during the robot's operation. The report may include documentation of the performance of the maintenance task, e.g., to demonstrate that it was successfully performed. The report may include metadata, such as the time at which a maintenance activity was performed or the location of the maintenance activity. The report may document the pre-maintenance state of a site on the structure (e.g., to demonstrate the need for the maintenance, or to demonstrate that a site was inspected but did not require maintenance).

After sending the final report to the base station, the robot enters a standby state (714). Just prior to entering the standby state, the robot may perform a pre-standby task, such as returning to a designated location and/or performing a charging function. For example, the robot may have standing instructions to return to a garage located on the structure prior to entering the standby mode. The pre-standby mode instructions may further include a charge command. The charge command can include parking the robot over an inductive charging port, instructing the robot to use a tool to plug into grid power, and/or positioning the robot such that it can receive electrical power from other sources (e.g., positioning the power such that built-in solar panels receive sun light). During the standby state, the robot enters a low-power mode. During the low-power mode, the robot's wireless transceiver remains active such that the robot can receive additional operating instructions. The controller of the robot also is at least partially powered during the low-power mode such that the controller can send and receive communications to and from the base station and/or other robots. Accordingly, if an instruction is received during the low-power, standby mode, the robot reactivates and method 700 is repeated.

In some embodiments, the robot is configured to operate autonomously. It may receive general operating instructions such as which area of a structure to examine, and which type of maintenance activities to perform. Alternatively, such instructions may be implicit e.g., the robot may be delivered to a structure via a truck, and then autonomously rove the structure, detecting areas in need of maintenance and performing the maintenance as needed. In some embodiments, the types of maintenance to be carried out can be implicitly defined by the tools and sensors present on the robot. The robot's roving route can be predefined based on the structure, can be defined by local conditions or sets of rules (e.g., always turn left, never repeat a section, etc.), can be a random or quasi-random path, etc. The robot may continue its autonomous activity for a defined amount of time, until a specified amount of the structure has been covered, etc.

Still referring to FIG. 7, as noted above, the operating instructions to the robot may include a variety of tasks and various combinations of tasks. The operating instructions may designate that multiple tasks are to be performed in a designated sequence. If multiple tasks are to be performed, the tasks may be performed by multiple robots or a single robot. The details of the tasks and how the tasks are carried out via the robots are described in further detail below.

The operating instructions may include an instruction for the robot to perform a detecting, sensing, and/or analyzing task (704). The detecting, sensing, and/or analyzing task may be for the purposes of generating data sets to report back to the base station or for local analysis by the controller of the robot (e.g., to determine whether or not detected stresses exceed a designated safety threshold). The detecting, sensing, and/or analyzing may be for the purposes of identifying areas of the structure requiring maintenance, which may be later performed by the robot. For example, during the detecting, sensing, and or analyzing, the robot may identify an area of rust buildup on the surface of the structure. After identifying the area, the rust may be removed by a cleaning operation (e.g., step 706) and then repainted (e.g., during 705). To accomplish the detecting, sensing, and/or analyzing task, the robot is configured with a sensor or a plurality of sensors (as discussed above with respect to robot 200, robot 300, robot 400, and robot 500).

The robot may include a sensor or a plurality of sensors to measure characteristics and identify features of the structure. The robot may be equipped with an ultrasound transducer. In such an arrangement, the transducer emits ultrasound waves into the structure, which at least partially reflect back towards the transducer for reception and analysis. The controller of the robot analyzes the ultrasound reflections. Localized structure stress levels, cracks, and other imperfections may be identified based on variances in the ultrasound reflections. The robot may be equipped with an eddy current sensor. The eddy current sensor generates and analyzes multi-frequency signals to determine localized structure stress levels, cracks, and other imperfections. A discussion of the use of eddy current sensors to inspect materials can be found in U.S. Pat. No. 7,206,706 to Wang et al. entitled "INSPECTION METHOD AND SYSTEM USING MULTIFREQUENCY PHASE ANALYSIS," dated Apr. 17, 2007. The robot may be equipped with a vibration sensor. The vibration sensor may be a piezo vibration sensor. The vibration sensor may be used to measure the vibration and resonance behavior of the structure. The robot may be equipped with an x-ray sensor configured to take x-ray images of the structure that may be beneficial in locating stress levels, cracks, and other imperfection of the structure. The robot may be equipped with a stress sensor. The stress sensor may be a resistive stress sensor that is temporarily affixed to a surface of the structure. The stress sensor may be used to measure compressive, tensile, and axial forces experienced by the structure at the location where the sensor is placed.

Additionally, the robot may be equipped with environmental sensors to measure atmospheric weather conditions (e.g., temperature, air pressure, humidity, wind direction, wind speed, etc.). The environmental sensors may measure underwater conditions. For example, if the structure is a bridge, an off-shore oil platform, or the like, the robot may be capable of underwater activities (e.g., robot 500). Accordingly, the robot may measure water temperature, water flow rate, and water flow direction. It should be understood that the sensors may measure non-water fluid characteristics. For example, a robot may be configured for operation in a non-water fluid (e.g., oil), and the sensors may measure characteristics of the non-water fluid.

The robot may be equipped with a camera. The camera may be mounted to an articulating tool arm of the robot such that the camera can be positioned to view different areas of the structure and of the surrounding environment. The camera may be an infrared camera or a visible light camera. The camera may be a multi-spectral camera or a polarized camera. The robot may have multiple cameras capable of focusing on different locations and/or providing a stereoscopic view. The robot may take images and/or videos of the structure and the surrounding environment. The images and/or videos may be processed by the controller to identify features (e.g., cracks, corrosion, cars/trucks/trains/people using the structure, etc.). The images and/or videos may be stored in a memory of the robot for later export or transmission to a server or a base station. The images and/or videos may be transmitted in a live or a near-live steam to a server or a base station. The live or near-live stream may be used to assist in providing a remote control capability of the robot. The operating instructions may include a command to take before and after pictures and/or videos for an additional task (e.g., a picture before a painting operation and a picture after the painting operation.

The robot may further be equipped with a sample gatherer and sample storage compartment. The gathered samples may be analyzed by onboard sample analyzer (e.g., composition sensors), or delivered to a base station for off-robot analysis. The robot can scrape and gather loose particles, crackling, and/or spalling from designated areas of the structure through a tool mounted on a tool arm of the robot. The tool may include a vacuum to capture and store the scraped or loose particles.

Still referring to FIG. 7, the operating instructions for performing a detecting, sensing, and/or analyzing task (704) may be for the purposes of identifying areas of the structure for the performance of an additional task and times for the performance of designated tasks. As discussed above, a sensor of the robot may be used to identify a specific location of the structure (e.g., a crack, a localized stress, corrosion, paint defects, etc.) where a further operation (e.g., cleaning, welding, painting, etc.) is desired. Further, the camera and/or stress sensor may be used to determine when the structure is being used or is under load (e.g., when a train is crossing a bridge). For certain operations, such as stress measurement, cold-working structure material, heat treating structure materials, etc., it may be beneficial to perform the operation while the structure is experiencing normal stresses. For other operations, such as cleaning and painting, where debris or paint overspray may fall from the structure, it may be beneficial to determine when the structure, or an area of the structure at risk of being hit or affected by the debris or overspray, is not being used or is not occupied so as not to damage objects or injure occupants of the structure. For example, when performing a repainting operation of a bridge, the sensors and cameras can be used to determine when vehicles and/or people are not crossing the bridge so as not to damage or injure the people with overspray of the paint. Continuing with the example, the robot may pause the repainting or cleaning operation if the robot determines that an object will enter an area affected by debris or paint overspray until the object leaves the area. Still further, feedback from the sensors may be used to identify potential particularly weak areas of the structure, areas of the structure at high risk for corrosion, and/or areas of the structure at high risk for the development of cracks to be regularly inspected/and or treated. Sensor feedback can be recorded at the same area of the structure over different periods of time. The recorded data can then be stored in a memory of the robot and/or transmitted to another robot or to a base station. The time correlated sensor readings can be used to calculate structure degradation (e.g., physical degradation, paint degradation, etc.), to demonstrate crack development and migration, to calculate structural and load models, to calculate estimated structural life, to calculate fatigue life (e.g., based on crack development, crack migration, crack depth, residual stresses, etc.).

Feedback from the sensors and/or cameras may be used during other maintenance operations (e.g., welding, cleaning, painting, etc.). The feedback can be used to lengthen or shorten a treatment time for the maintenance task. For example, the sensor feedback may be used to determine when the appropriate amount of peening has been performed in a later peening operation. Additionally, the sensor feedback can be used to modify an on-going operation. For example, sensor feedback may be used to monitor internal stresses of the structure during crack migration and make changes to the crack migration operation in response to the sensor feedback.

The operating instructions may include an instruction for the robot to perform a painting task (705). Accordingly, the robot can be equipped with a paint sprayer, a self-feeding paint roller, or another painting tool. The painting task can correspond to a spot painting task, in which the robot roves the structure and repaints certain areas based on sensor feedback. Alternatively the painting task can correspond to an area painting task, in which an entire area of the structure (or the entire structure) is to be repainted. The paint used by the robot may be a primer, a latex-based paint, an anti-graffiti paint, an anti-climb paint, an anti-fouling paint, an anti-corrosion paint, and/or an insulating paint. As discussed above, cameras and sensors on the robot may be used during a painting operation to select an appropriate time to paint and/or pause and restart the painting operation to avoid damaging objects on the structure or injuring people occupying the structure.

The operating instructions may include an instruction for the robot to perform a cleaning task (706). The cleaning task may be performed prior to another task (e.g., the painting task of 705, the welding task of 708, etc.). The cleaning task may involve the cleaning of the surface of the entire structure or a designated area of the structure (e.g., at an area to be welded or repainted). The surface cleaning may remove a protective coating (e.g., paint), an area of corrosion (e.g., a rusted portion of the structure), or a surface layer of the structure (e.g., to prepare the area of the surface layer for inspection or welding). The robot performs the cleaning task through any number of tools attached to a tool arm of the robot. The robot may be configured to have an abrasive blaster tool (e.g., a sand blasting tool) attached to the tool arm. Alternatively, the robot is configured with an abrasive grinding tool attached to the tool arm. In yet another alternative, the robot is configured with a brush attached to the tool arm.

Referring again to FIG. 7, the operating instructions may include an instruction for the robot to perform a crack and dislocation migration or prevention task (707). One way the robot may perform this task is through a peening operation. The robot may perform a peening operation to prevent the formation of cracks at an area of the structure. Generally, a peening operation works to relieve tensile stress in metal and replace the tensile stress with a compressive stress. Because cracks are more apt to form under tensile stress, the peening operation reduces the risk of crack formation in the material. The peening operation may target the surface and/or the subsurface of the material of the structure. The peening may be performed by repeatedly impacting the surface of the structure to produce a compressive residual layer that modifies the structure of the material of the structure. The peening operation may be performed mechanically. To accomplish the mechanical peening operation, the robot may be equipped with a hammer to repeatedly strike the surface of the structure. Alternatively, the robot may be equipped with a media blasting gun that emits shot (ceramic, steel, glass, etc.) at the structure. The peening operation may alternatively be performed via a laser. Accordingly, the robot may be equipped with a laser to perform laser peening on the structure. Accordingly, the robot can perform targeted hardening of an area of the structure by emitting a laser beam into the area of the structure. The laser beam is emitted in pulses that produce shockwaves through the structure at the area. The shockwaves cause residual compressive stresses in the structure, which may improve the strength and/or fatigue life of the structure. The laser peening may be performed after an energy absorbing coating (e.g., a dark colored paint) is provided in a painting process (e.g., painting of 705). The details of using a laser to perform a peening operation are discussed in U.S. Pat. No. 6,288,353 to Dulaney et al., entitled "MOBILE LASER PEENING SYSTEM," dated Sep. 11, 2001.

The robot may be equipped to perform other area treating of structure materials to prevent crack formation. For example, the robot may be equipped with an electric and/or magnetic field generator to performed localized heating of structure materials (e.g., inductive heat generation) for heat treatment purposes. As an additional example, the robot may be equipped with an ultrasound emitter. The ultrasound emitter transfers mechanical energy to the structural material to perform a work hardening operation similar to the peening operations discussed above.

The robot may also be equipped with a drill to be used in mitigating the migration of existing cracks. In such a configuration, the robot can stop the spreading of a crack by drilling at an edge of a crack. The drilled hole increases the radius of curvature of the crack thereby reducing the maximum stresses caused by the crack by spreading the stresses of a crack over a greater area. The structure strengthening task may be a crack dislocation and/or migration task. To perform the task on a designated crack in the structure, the robot requires location information that provides the location of the crack to the robot. The location information may be provided with the operating instructions (e.g., an operator can instruct the robot to repair a specified crack at a specified location). Alternatively, the location information may be gathered by the robot or another robot during a structure analysis via sensors or a camera (e.g., 704).

The operating instructions may include an instruction for the robot to perform a welding task (708). The robot may be configured to weld various metal structures. Depending on the configuration, the robot performs arc welding with consumable or non-consumable electrodes, oxyfuel gas welding, tungsten inert gas welding, friction stir welding, resistance welding, laser beam welding, electron beam welding, or a form of solid-state welding. The operating instructions may instruct the robot to insert filler material into located cracks by performing welds. The filler material may be provided from a wire of metal, which is used to fill small cracks and holes, or may be a larger, custom plate, which is welded into place to fill larger gaps in the structure's material. The robot may be instructed to perform localized welding or melting operations to resurface material after a cleaning operation (e.g., cleaning performed in 706) and/or prior to a painting operation (e.g., painting performed in 705). The robot may also perform the welding task to relieve, create, and/or control stress levels in the surface and subsurface of the structure.

The operating instructions may include an instruction for the robot to perform a tool change (709). As discussed above with respect to robot 200, robot 300, robot 400, and robot 500, the robot may include at least one tool arm. The tool arm can be equipped with a variety of tools and sensors. Some operating instructions may call for the performance of a variety of tasks. Accordingly, the robot may need to change tools during performance of the operating instructions if a greater number of tools is required than tool arms available. The spare tools and equipment may be stored on the robot. In such an arrangement, the robot performs the tool change at the worksite. Alternatively, the spare tools and equipment may be stored on another robot. In this case, the robot will communicate with the another robot to coordinate the tool change. In yet another alternative, the spare tools and equipment may be stored at a specific location on or near the structure (e.g., a robot storage space, the base station, etc.). In such a setup, the robot roves to the storage location to perform the tool change, and then the robot returns to the worksite to perform the task.

The operating instructions may include an instruction for the robot to perform a recharging operation (710). During execution of the operating instructions, the robot may need to recharge its batteries or the tool batteries. The recharging operation may be automatically triggered by the controller of the robot if battery levels fall below a level of charge. The robot may perform the recharging operation in a variety of ways. In some arrangements, the robot is equipped with a solar panel capable of recharging the robot's batteries. In such an arrangement, the robot moves to an area of the structure such that the solar panels are positioned in sunlight. In other arrangements, the robot instructs a power supply robot to provide a charge. The power supply robot is equipped with power storage devices (e.g., batteries, capacitors, etc.) that can be used to recharge the batteries of the robot. In another alternative charging scenario, the robot can recharge its batteries by roving to a charging station. The charging station provides grid power to the robot through inductive charging (wireless charging) or a wired electrical connection. In another arrangement, the robot can receive a charge from another robot.

The operating instructions may include an instruction for the robot to communicate with other robots (711). As discussed above, many tasks can utilize multiple robots. The multiple robots may cooperate in working, sharing data, and passing data to the base station (e.g., passing data to servers). The robots may perform multiple tasks in a coordinated sequence (e.g., a first robot cleans an area of a surface of the structure, a second robot welds the area, and a third robot paints the area). Alternatively, robots may perform the same task in parallel (e.g., multiple robots inspect different areas of the same structure to perform a structure-wide inspection faster than a single robot can provide). Still, in an alternative setup, robots may perform independent tasks simultaneously (e.g., a first robot inspects, a second robot welds, a third robot carries additional tools and supplies, a fourth robot provides recharging services to the other robots, etc.). Still further, multiple robots can perform the same task at the same time. For example, while fixing a deep crack in a thick material, a first robot can heat the material from a first side while a second robot simultaneously heats the same material from an opposite side. In another example of two robots performing the same task at the same time, two robots may be positioned on opposing ends of a turnbuckle that needs to be shortened or lengthened, and the distance between the two robots may be monitored to determine when the turnbuckle has be adjusted to an appropriate length. In another alternative, multiple robots may each carry or support a different portion of a component, such as a tie rod or a cable, that is not capable of being supported or carried by a single robot. In each arrangement, it may be necessary for the various robots to communicate with each other and to pass coordinated information on to the base station or to a server. Accordingly, the robots each are equipped with wireless transceivers capable of transmitting and receiving instructions directly from other robots. Alternatively, inter-robot communications are coordinated through a base station such that an instruction sending robot first sends an instruction to the base station, where the instruction is processed, automatically by a computing system or by a human operator, and relayed to the recipient robot.

Although the above discussion primarily focuses on bridge cleaning robots (e.g., robots 103), it should be understood that the above discussed systems and methods may be used on non-bridge structures. For example, robots 103 may be used to inspect, clean, and repair structures such as power plants, commercial skyscrapers, residential buildings, and off-shore oil platforms, to recite several examples. The robots may be used on exterior surfaces of structures, interior surfaces of structures, or within hollow structures. Further, the above discussed systems and methods may be applied to inspect, clean, and repair other objects and devices, such as airplanes, spacecraft, boats, trains, automobiles, and other devices. Any sort of object in need of inspection, repair, and/or cleaning may utilize the above discussed systems and methods.

The construction and arrangement of the systems and methods as shown in the embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. The elements and/or assemblies of the enclosure may be constructed from any of a wide variety of materials that provide sufficient strength or durability, and in any of a wide variety of colors, textures, and combinations. Any embodiment or design described herein not necessarily to be construed as preferred or advantageous over other embodiments or designs. Accordingly, all such modifications are intended to be included within the scope of the present inventions. The order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other embodiments without departing from scope of the present disclosure or from the spirit of the appended claims.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures, and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps, and decision steps.

What is claimed is:

1. A method of performing a maintenance task on a structure via a robot, the method comprising:
    moving to an area of the structure through a drive system of the robot;
    detecting a characteristic of a portion of the structure through a sensor of the robot;
    in response to detecting the characteristic, identifying a maintenance task including treating a defect at an area of the structure and painting the area of the structure;
    performing a first portion of the maintenance task through a first tool mounted to a tool arm of the robot, wherein the first portion includes treating the defect;
    performing a tool change from the first tool to a second tool;
    performing a second portion of the maintenance task through the second tool mounted to the tool arm of the robot, wherein the second portion includes painting the area of the structure; and
    documenting the performance of the maintenance task.

2. The method of claim 1, further comprising receiving an operating instruction via a transceiver of the robot, wherein the operating instruction includes an indication of the maintenance task.

3. The method of claim 2, further comprising analyzing the operating instruction at a processor of the robot, wherein the analyzing includes identifying an area of the structure where the maintenance task is to be performed.

4. The method of claim 1, wherein the documenting comprises delivering a report to a base station after completing the maintenance task.

5. The method of claim 4, wherein the report includes at least one of a time associated with the performance of the maintenance task and a location of the portion of the structure.

6. The method of claim 4, wherein the report further includes characterization information on the pre-maintenance state of a portion of the structure.

7. The method of claim 1, wherein the documenting comprises characterizing the portion of the structure after performance of the maintenance task through a sensor of the robot.

8. The method of claim 1, further comprising mounting the first tool to the tool arm of the robot.

9. The method of claim 8, wherein the mounting step is performed after removing an unnecessary tool from the tool arm of the robot.

10. The method of claim 1, wherein the defect corresponds to an area of corrosion in the structure, and the maintenance task corresponds to treating the area of corrosion.

11. The method of claim 1, wherein the sensor is one of an ultrasound sensor, an eddy current sensor, a vibration sensor, and an x-ray sensor.

12. The method of claim 1, wherein the sensor is a stress sensor.

13. The method of claim 12, further comprising affixing the stress sensor to a surface of the structure.

14. The method of claim 1, further comprising gathering a sample of the structure.

15. The method of claim 1, wherein the defect is a crack.

16. The method of claim 15, further comprising locating the crack in the structure through a sensor on the robot.

17. The method of claim 16, further comprising drilling a portion of the crack to relieve a stress in the structure.

18. The method of claim 16, further comprising performing a peening operation on the area of the structure surrounding the crack to relieve a stress in the structure.

19. The method of claim 16, further comprising filling the crack with a welding operation.

20. The method of claim 16, further comprising heat treating the area of the structure surrounding the crack.

21. The method of claim 1, wherein the area of the structure is a first area, and wherein the method further comprises determining that a second area of the structure at risk of being affected by paint overspray will become occupied by an object during the painting step.

22. The method of claim 21, further comprising pausing the painting step in response to determining that the second area of the structure will become occupied by the object until the object leaves the second area.

23. The method of claim 1, wherein the characteristic corresponds to a defect located at the area of the structure.

24. The method of claim 1, wherein the painting the area of the structure occurs after treating the defect.

* * * * *